United States Patent [19]

Knapp

[11] Patent Number: 4,554,125

[45] Date of Patent: Nov. 19, 1985

[54] METHOD OF MAKING A STOPPER FOR A STERILE FLUID CONTAINER

[75] Inventor: Julius Z. Knapp, Somerset, N.J.

[73] Assignee: Schering Corporation, Kenilworth, N.J.

[21] Appl. No.: 476,075

[22] Filed: Mar. 17, 1983

[51] Int. Cl.[4] .................. B29H 9/00; B29C 11/00
[52] U.S. Cl. ................................ 264/266; 156/245;
156/307.7; 215/247; 215/364; 264/268;
264/320; 264/325
[58] Field of Search .............. 264/263, 266, 267, 236,
264/248, 322, 320, 325; 215/247, 364; 428/519;
156/245, 307.7

[56] References Cited

U.S. PATENT DOCUMENTS

| | | | |
|---|---|---|---|
| 2,680,531 | 6/1954 | Underwood | 215/38 |
| 2,698,272 | 12/1954 | Clapp et al. | 154/110 |
| 3,092,278 | 6/1963 | Jarnhall | 215/37 |
| 3,198,368 | 8/1966 | Kirkland et al. | 215/37 |
| 3,313,439 | 4/1965 | Robinson | 215/37 |
| 3,424,329 | 1/1969 | Hershberg et al. | 215/37 |
| 3,470,291 | 9/1969 | Johnson | 264/292 |
| 3,546,746 | 12/1970 | Johnson | 18/29 |
| 3,552,591 | 1/1971 | Wimmer | 215/37 |
| 3,606,958 | 9/1971 | Coffman | 220/63 |
| 3,760,969 | 9/1973 | Shimamoto et al. | 215/37 |
| 3,898,046 | 8/1975 | Ikeda et al. | 23/259 |
| 4,133,927 | 1/1979 | Tomoda et al. | 428/215 |
| 4,172,875 | 10/1979 | Beijen et al. | 264/550 |
| 4,254,884 | 3/1981 | Maruyama | 215/247 |

FOREIGN PATENT DOCUMENTS

| | | | |
|---|---|---|---|
| 0028411 | 5/1981 | European Pat. Off. | 215/247 |
| 2701627 | 7/1978 | Fed. Rep. of Germany | 264/267 |
| 1367338 | 9/1974 | United Kingdom . | |

Primary Examiner—W. E. Hoag
Assistant Examiner—M. McGurk
Attorney, Agent, or Firm—Serle I. Mosoff; Warrick E. Lee, Jr.

[57] ABSTRACT

A molding process for manufacturing laminated stoppers having an elastomer core and thin thermoplastic liner where a sheet of thermoplastic liner material having an elongation of at least 450% and the vulcanizable elastomer core material are placed in a mold and molded at a temperature above the vulcanization temperature of the elastomer core but below the crystalline molding point of the thermoplastic liner.

4 Claims, 5 Drawing Figures

METHOD OF MAKING A STOPPER FOR A STERILE FLUID CONTAINER

The present invention relates to stoppers for containers of injectable fluids. The vast majority of such stoppers presently in use are made of elastomer, such as natural rubber or butyl rubber. Rubber stoppers have the advantage of having a high degree of compliance, i.e. flexibility or lack of stiffness, necessary to provide a tight fit in the opening of a container. High stopper compliance is particularly important for mass-produced glass containers, since such containers cannot be formed to close tolerance. Hence the stopper must be sufficiently pliable to provide a tight sterility barrier over a fairly wide range of opening sizes.

Rubber stoppers have certain disadvantages. One disadvantage is their tendency to cause particles or flakes to enter the solution. Upon prolonged storage, the rubber may react with the sterile fluid causing the rubber to form particulates which are shed into the fluid. Furthermore, it is difficult to completely clean extraneous particles from rubber stoppers. Attempts to thoroughly clean particles from the surface of rubber abrade the surface. These abrasions can deteriorate into particulates upon prolonged storage. Also, molded rubber stoppers stick to the mold during the manufacturing process unless a mold release agent is coated onto the mold. However, if gaps occur in the mold release coating small tears will form in the rubber when it is pulled away from the mold. These tears can also promote the formation of particulates upon prolonged storage.

Prior art attempts to alleviate these problems consisted of spray coating or bonding thermoplastic onto the surface of the stopper destined to contact the injectable solution. However, spray coating with a variety of surface finishes proved to be an inadequate solution because the spray-coated materials flaked away from the elastomeric substrate during long-term storage, producing particulate contamination. Any adhesive used to bond thermoplastic to the rubber can also contaminate the solution by migrating through the thermoplastic. This is a problem when the stopper is penetrated by the cannula of a hypodermic syringe in a multidose bottle of injectable fluid. Furthermore, if the laminated thermoplastic is thick, or if the thermoplastic chosen is not sufficiently flexible, the compliance of the stopper is reduced, potentially affecting the sterility barrier.

The present invention provides a stopper having a very thin layer of thermoplastic laminated to an elastomeric core without adhesive. The thermoplastic layer is manufactured relatively free of punctures, isolating the elastomer from the injectable solution. The stoppers are easy to clean and highly resistant to formation of particulates. The inventive stopper has substantially the same degree of compliance as the elastomer core and can be manufactured very easily and inexpensively. Furthermore, since the elastomer is well isolated from the solution by the thermoplastic barrier, it is possible to choose elastomers that would not be usable in direct contact with the solution. Hence, cheaper or more flexible elastomers may be chosen. One aspect of the invention comprises a method for making a stopper to hold fluid in a container, said stopper having a thin layer of thermoplastic laminated without adhesive to form a surface intended to contact the fluid comprising:

(a) providing a first mold half having a concavity and a second mold half opposite the concavity, (b) disposing a thin sheet of thermoplastic between the mold halves and vulcanizable elastomer between the thermoplastic and the second mold half, the thermoplastic having an elongation of at least 450% and a crystalline melting point higher than the minimum vulcanizing temperature of the elastomer, (c) heating the mold halves to a temperature that is within the softening range and below the crystalline melting point of the thermoplastic and above the minimum vulcanizing temperature of the elastomer, (d) pressing the heated mold halves toward each other with pressure sufficient to force elastomer into the concavity while simultaneously forming thermoplastic against the surface of the concavity, and (e) holding the mold halves in pressed position for a time sufficient to vulcanize the elastomer.

A second aspect of the invention comprises a stopper for holding fluid in a container comprising:

(a) a body of vulcanized elastomer having a convex surface and laminated to the convex surface without adhesive, (b) a thin layer of thermoplastic to form a surface intended to contact the fluid and the side of an opening in the container.

DETAILED DESCRIPTION OF THE INVENTION

Figure 1:
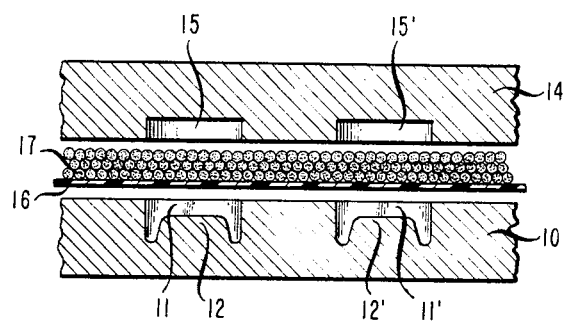
FIG. 1 schematically illustrates apparatus for forming stoppers in accordance with the invention prior to molding the stoppers with the mold halves open.
Figure 2:
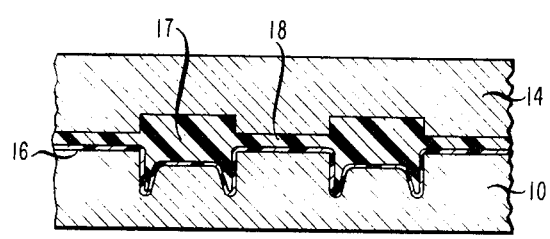
FIG. 2 illustrates the apparatus of FIG. 1 with the mold halves closed.

Apparatus used for making stoppers in accordance with the invention is schematically illustrated in FIGS. 1 and 2. Ordinary molding apparatus for elastomeric materials, well-known in the art and currently used to make conventional rubber stoppers, may be used. A first mold half 10 having at least one concavity 11 is provided. It is preferred to provide a mold half having a multiplicity of concavities so that many stoppers may be molded simultaneously. Two concavities 11 and 11' are shown in the FIGS. 1 and 2. When forming stoppers for use on vials of injectable fluid, it is preferred that there be convexities 12 and 12' within the concavities. Hence, concavities 11 and 11' terminate in annular protrusions. This will provide a stopper having the shape shown in FIG. 3.

A second mold half 14 is provided opposite concavities 11 and 11' in first mold half 10. Second mold half 14 may have circular concavities 15 and 15' opposite concavities 11 and 11' in first mold half 10.

A sheet of thermoplastic 16 is disposed between the mold halves. The thermoplastic has an elongation of at least about 450%, i.e., the thermoplastic is capable of stretching to at least about 5½ times its original length without fracturing.

Vulcanizable elastomer 17 is disposed between sheet 16 of thermoplastic and second mold half 14. The elastomer may be in the form of granules as shown in FIG.

1 or in the form of one or more sheets of calendered unvulcanized elastomer. Preferred vulcanizable elastomers are natural rubber and butyl rubber. The vulcanizable elastomer vulcanizes when its temperature is raised above a certain minimum vulcanizing temperature and maintained at that temperature for a vulcanizing period of time. The elastomer and thermoplastic are chosen so that the crystalline melting point of the thermoplastic is higher than the minimum vulcanizing temperature of the elastomer. For example, typical polypropylene copolymers useful in practicing the invention have crystalline melting points of about 170° C. An elastomer useful with this material is butyl rubber having minimum vulcanizable temperature of 140° C.

With mold halves 10 and 14, thermoplastic sheet 16 and vulcanizable elastomer 17 disposed as shown in FIG. 1, the mold halves are heated to a temperature that is within the softening range and below the crystalline melting point of the thermoplastic and above the minimum vulcanizing temperature of the elastomer. If the materials described in the previous paragraph are used, the mold halves would be heated to a temperature between 140° and 150° C., more preferably about 145° C.

The mold halves are then pressed toward each other by means not shown with pressure sufficient to force elastomer into concavities 11 and 11'. When this is done, the elastomer pushes the thermoplastic ahead of it into the concavities, stretching the thermoplastic and forming it against the surface of the concavities. FIG. 2 shows the mold halves in pressed position. The mold halves are held in the pressed position of FIG. 2 for a time sufficient to vulcanize the elastomer. The mold halves are then opened and the stoppers are cut away from the web 18 of excess elastomer and thermoplastic to yield stoppers having the shape shown in FIG. 3. It has been found that the layer of thermoplastic makes an excellent release agent rendering removal of stoppers from the mold concavities very easy without generating small tears in the elastomer or thermoplastic.

Preferably the space between the mold halves is evacuated prior to pressing the mold halves toward each other to minimize air bubbles in the finished product. Evacuation to an absolute pressure below 0.2 atmospheres is preferred. The vacuum may be attained by using a vacuum rubber press, well known in the art.

Figure 3:
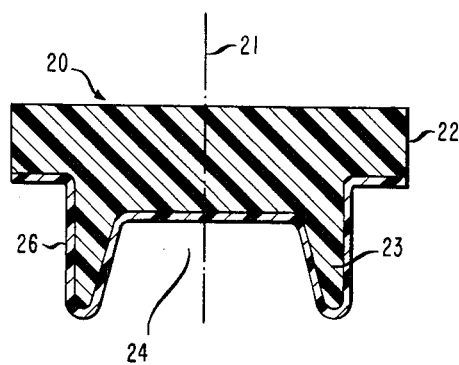
FIG. 3 is a cross sectional view of a stopper in accordance with the invention.

FIG. 3 is a cross sectional view of a preferred shape of a stopper formed in accordance with the invention. Stopper 20 is circular when viewed from the top of FIG. 2; hence rotation of the cross section shown in FIG. 3 about axis 21 generates the stopper in three dimensions. Stopper 20 has an elastomeric flattened cylindrical top 22 with an annular protrusion 23 from top 22, i.e. a convex surface, having a concavity 24. A layer of thermoplastic 26 is laminated without adhesive to the elastomer on the outside of annular protrusion 23 and on the inside of concavity 24. The exact mechanism by which the thin layer of thermoplastic is laminated to the elastomer without use of adhesive is not known. However, while not wishing to be bound by any particular theory, it is believed that at the vulcanizing temperature of the elastomer and within the softening range of the thermoplastic, the thermoplastic attains increased molecular mobility, without actually experiencing crystalline melting. This increased molecular mobility, combined with the molding pressure, is believed to generate an adhesive interaction between the elastomer and the thin sheet of thermoplastic.

The choice of thermoplastic is important. The thermoplastic must have an elongation of at least 450 percent and should laminate to the elastomer at the molding temperature and pressure without adhesive or special preparative treatment. Teflon and nylon are not acceptable because they fail to meet either of these criteria. Polyethylene homopolymer is acceptable, but not preferred because it cannot withstand the sterilization temperature of 121° C. to which it is desirable to subject the stopper prior to use. Polypropylene homopolymer is acceptable but not preferred because it can become brittle upon long-term storage or exposure to radiation. The preferred thermoplastic is a 0.0035 inch (0.009 cm) thick or less sheet of a propylene copolymer, more preferably a copolymer formed by copolymerizing from 5 to 9 percent ethylene with from 91 to 95 percent propylene and having at least 500% elongation. Such copolymers are readily available on the market from Shell and Hercules.

The thickness of the thermoplastic sheet should be the minimum required to avoid rupture during the stretching that takes place in the forming step. Choosing thicker sheets reduces the degree of compliance, and hence the sealing ability, of the stopper. For stoppers shaped as shown in FIG. 3 having outside diameter of cylinder 22 of about 13 mm, a thickness of 0.0035" (0.009 cm) is adequate and it is believed that even lower thicknesses would suffice. For larger stoppers, the thickness of the thermoplastic may be higher, but it is highly desirable that the thickness not exceed 0.0075" (0.02 cm). Of course, after forming, the thermoplastic laminated to the elastomer will be thinner than the initial thickness of the thermoplastic sheet.

Preferably, the polymer begins to soften at about 135° to 145° C. (more preferably 140° C.) and has crystalline melting point of from about 150° C. to about 175° C. (more preferably about 165° to about 170° C.). The elastomer chosen must have a minimum vulcanization temperature below the crystalline melting point of the thermoplastic. Finding a suitable vulcanizable elastomer is easy given the wide variety of choices available in natural and butyl rubber.

The temperature to which the mold halves are heated is not critical so long as the temperature is (a) low enough to be below the crystalline melting point of the thermoplastic, (b) high enough to be within the softening range of the thermoplastic, and (c) high enough to be above the minimum vulcanization temperature of the elastomer.

For the materials described above, it is preferable to heat the mold halves to from about 140° to 148° C. The pressure applied to the mold halves is not critical so long as it is sufficient to mold the elastomer in the conventional manner, since the elastomer-molding pressure is far more than that required to form the softened thermoplastic.

Sharp edges and corners in the mold design should be avoided, since they concentrate strain in the thermoplastic material. For best results, all corners should have a minimum radius of 0.0010" (0.0025 cm).

Figure 4:
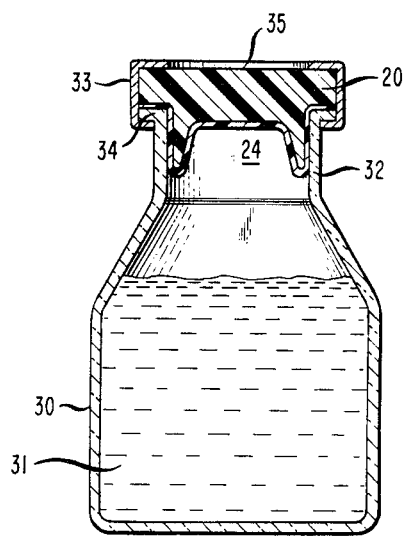
FIG. 4 is a cross section of a bottle of injectable fluid stoppered with the stopper of the invention.

FIG. 4 illustrates the stopper of FIG. 3 in place in the neck of a bottle of injectable fluid. Bottle 30 containing injectable fluid 31 has neck 32. Disposed in neck 32 is stopper 20 from FIG. 3, a thin metal seal 33 is crimped over stopper 20 and flange 34 to hold the stopper in place. A thin portion 35 of stopper 20 is located above concavity 24. To withdraw injectable fluid from bottle 30 one penetrates thin portion 35 with the cannula of a hypodermic syringe and draws fluid into the barrel of the syringe in a manner well-known in the art.

Figure 5:
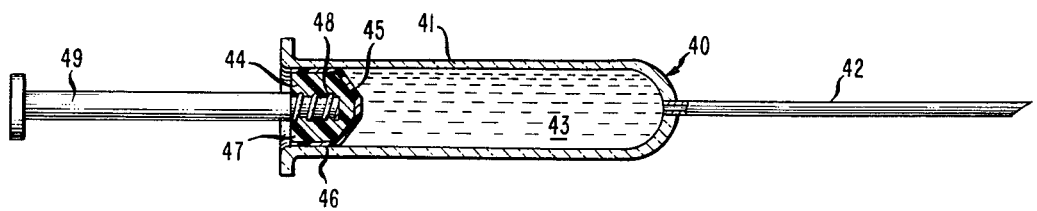
FIG. 5 is a cross sectional view of a hypodermic syringe having a stopper in accordance with the invention.

FIG. 5 illustrates a hypodermic syringe having a stopper formed in accordance with the invention. Syringe 40 has hollow barrel 41 and cannula (i.e., hollow needle) 42. Injectable fluid 43 is disposed within barrel 41. Stopper 44 holds the fluid in the barrel. Surface 45, contacting the fluid, and the surface 46, contacting the bore of barrel 41, are covered with a thin sheet of thermoplastic laminated to core of elastomer 47. The surface of the stopper outside the fluid has an engagement means 48 such as an internal thread for engaging plunger rod 49. During storage, the pre-filled disposable syringe of FIG. 5 would have an elastomeric needle guard (not shown) covering and stoppering cannula 42 in a manner well-known in the art.

For some applications, it may be desirable to laminate a sheet of thermoplastic to both sides of the stopper. This could be accomplished by disposing a second sheet of thermoplastic (not shown) between elastomer 17 and mold half 14 in FIG. 1. The resulting stopper, having thermoplastic laminated to its top surface, would be easier to clean and to handle with automatic machinery.

It can be seen that stoppers made in accordance with the invention have several advantages over prior art rubber stoppers and prior art rubber stoppers having thermoplastic laminated to a rubber core.

A. The high degree of compliance of rubber or other elastomer is not lost, because the layer of thermoplastic is very thin.

B. The thermoplastic is laminated to the elastomeric core without adhesive; hence the possibility of contaminating the solution with adhesive or adhesive component is eliminated.

C. It is very easy to clean the thermoplastic surface of particulates without causing tears in the elastomer.

D. The thermoplastic laminate is much less reactive with the solution than rubber, allowing for a much longer storage without contamination of the solution with particles of rubber.

E. During manufacture, the thermoplastic and elastomer are molded simultaneously, thereby eliminating the need to initially mold the thermoplastic and place the molded thermoplastic inserts into the mold for the elastomer as required by some prior art lamination methods.

F. Since the elastomer is isolated from the solution, it is possible to choose elastomers that are not compatible with the solution, such as elastomers that are cheaper and/or more pliable.

What is claimed is:

1. A method for making a stopper to hold fluid in a container, said stopper having a thin layer of thermoplastic laminated without adhesive to form a surface intended to contact the fluid comprising:
    (a) providing a first mold half having a concavity and a second mold half opposite the concavity,
    (b) disposing a sheet of thermoplastic between the mold halves and vulcanizable elastomer between the thermoplastic and the second mold half, the thermoplastic having an elongation of at least 450% and a crystalline melting point higher than the minimum vulcanizing temperature of the elastomer,
    (c) heating the mold halves to a temperature that is within the softening range and below the crystalline melting point of the thermoplastic and above the minimum vulcanizing temperature of the elastomer,
    (d) pressing the heated mold halves toward each other with pressure sufficient to force elastomer into the concavity while simultaneously forming thermoplastic against the surface of the concavity, and
    (e) holding the mold halves in pressed position for a time sufficient to vulcanize the elastomer.

2. The method of claim 1 wherein the elastomer is selected from the group consisting of natural rubber and butyl rubber.

3. The method of claim 1 wherein the thermoplastic is selected from the group consisting of polypropylene and polypropylene copolymers having an elongation of at least 500% and a crystalline melting point of about 150° to 175° C.

4. The method of claim 3 wherein the vulcanizable elastomer is selected from the group consisting of natural rubber and butyl rubber and wherein the mold halves are heated to a temperature of between 140° and 150° C.

* * * * *